United States Patent [19]

Lombardi et al.

[11] 4,269,771
[45] May 26, 1981

[54] TOTAL SYNTHESIS OF 7-OXO-4-THIA-1-AZABICYCLO-[3,2,0]-HEPTANE-2-CARBOXYL DERIVATIVES USEFUL AS β-LACTAMASE INHIBITORS AND ANTIBACTERIAL AGENTS

[75] Inventors: Paolo Lombardi; Giovanni Franceschi; Federico Arcamone, all of Milan, Italy

[73] Assignee: Farmitalia Carlo Erba, Milan, Italy

[21] Appl. No.: 93,603

[22] Filed: Nov. 13, 1979

[30] Foreign Application Priority Data

Apr. 6, 1979 [GB] United Kingdom ............... 12168/79

[51] Int. Cl.³ .......................................... C07D 499/00
[52] U.S. Cl. .............................. 260/245.2 R; 424/270
[58] Field of Search ...................................... 260/245.2

[56] References Cited

U.S. PATENT DOCUMENTS

| | | | |
|---|---|---|---|
| 3,905,965 | 9/1975 | Martel et al. | 260/245.2 |
| 4,053,468 | 10/1977 | Holden | 260/245.2 |
| 4,155,912 | 5/1979 | Menard | 260/245.2 |

FOREIGN PATENT DOCUMENTS 866845 12/1978 Belgium .

*Primary Examiner*—Nicholas S. Rizzo

*Attorney, Agent, or Firm*—Stevens, Davis, Miller & Mosher

[57] ABSTRACT

A process is disclosed for the preparation of compounds of formula I:

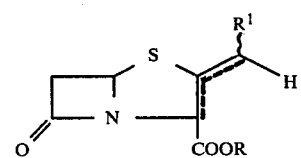

wherein R is hydrogen, lower alkyl, trichloroethyl, benzyl, p-nitrobenzyl, acetoxymethyl, pivaloyloxymethyl, phthalidyl, or a —CH(CH$_3$)OCOOEt group;

$R^1$ is —CH$_2$OH, —CHO, —CH$_2$SH, —CH$_2$NH$_2$, —CH$_2$OCOR$^2$, —COOR$^2$, —CH$_2$NHCOR$^2$, —CH$_2$OR$^3$, or —CH$_2$SR$^4$ where $R^2$ is a lower alkyl, aryl or a heterocyclic ring, $R^3$ is a lower alkyl, benzyl, or trityl, and $R^4$ is a five- or six-member heterocyclic ring containing one or more heteroatoms, which comprises reacting a 4-acetoxy azetidinone with a β-thioketoester to form a mixture, reacting said mixture with thionyl chloride followed by reaction with a phosphine and a base, ozonolyzing and heating to obtain the compounds of formula I.

2 Claims, No Drawings

TOTAL SYNTHESIS OF 7-OXO-4-THIA-1-AZABICYCLO-[3,2,0]-HEPTANE-2-CARBOXYL DERIVATIVES USEFUL AS β-LACTAMASE INHIBITORS AND ANTIBACTERIAL AGENTS

The present invention relates to the total synthesis of new and novel compounds of the formula (1):

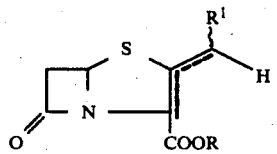

where R is hydrogen, lower alkyl, trichloroethyl, benzyl, p-nitrobenzyl, acetoxymethyl, pivaloyloxymethyl, phthalidyl or a group of formula —CH(CH$_3$)OCOOEt;

$R^1$ is —CH$_2$OH, —CH$_2$OCOR$^2$, —CH$_2$OR$^3$, —COOR$^2$; —CHO, —CH$_2$SH, —CH$_2$SR$^4$, —CH$_2$NH$_2$, or —CH$_2$NHCOR$^2$;

$R^2$ is a lower alkyl, aryl, or a heterocyclic moiety;

$R^3$ is a lower alkyl, benzyl, or trityl; and $R_4$ is a five- or six-member heterocyclic ring containing one or more heteroatoms.

Compounds of formula (1), as chiral molecules, have been claimed in our British Application No. 45966/78 and our U.S. Application Ser. No. 66,333, filed Aug. 14, 1979. They are potent irreversible inhibitors of different β-lactamases as illustrated by a dramatic reduction of the MIC value of ampicillin against β-lactamase-producing bacteria. They also are endowed with antibacterial activity.

According to the present invention, the 4-acetoxy azetidinone (2) (K. Clauss, D. Grimm and G. Prossel, *Justus Liebigs Ann. Chem.*, 539 (1974)), which is known to give easy nucleophilic displacements at the position 4 by means of "soft" bases or acids such as thiols, thioenols, or carbinols (K. Clauss, D. Grimm, and G. Prossel, *ibidem;* W. A. Szako, *Aldrichimica Acta* 10, 23 (1977); P. H. Bentley, P. D. Berry, G. Brooks, M. L. Gilpin, E. Hunt and I. I. Zomaya, *J.C.S. Chem. Comm.*, 1977, 748; A. Suarato, P. Lombardi, C. Galliani, and G. Franceschi, *Tetrahedron Lett.*, 1978, 4059) is treated with a β-thioketoester of the type R$^1$CH$_2$—C(SH)=CHCOOEt, where R$^1$ is a group as defined above, in the presence of a base such as NaHCO$_3$, Na$_2$CO$_3$, K$_2$CO$_3$, NaOH, KOH, Et$_3$N, and the like, in a suitable solvent such as H$_2$O, tetrahydrofuran, dimethylformamide, Me$_2$CO, hexamethylphosphoramide, and their mixtures.

Compound (3), obtained in this way, is condensed with a suitable derivatives of the glyoxylic acid of the type CHOCOOR, where R is a lower alkyl, trichloroethyl, benzyl, p-nitrobenzyl, benzhydryl, acetoxymethyl, pivaloyloxymethyl, trimethylsilyl, or dimethyl-t-butylsilyl, either at a temperature between 40° and 100° C. or at room temperature in the presence of a base such as Et$_3$N, pyridine, and the like.

Subsequent chlorination of the resulting diastereoisomeric carbinols (4), using preferably thionyl chloride and a base such as pyridine at a temperature ranging from −78° to 0° C. affords the chlorides (5) which are transformed into the phosphorous ylid (6) by means of triphenylphosphine and a base such as pyridine or 2,6-lutidine at a temperature around 25°–50° C.

Careful ozonolysis of compound (6) in the presence of an acid such as CF$_3$COOH as an ylid protection, yields the phosphorane (7), after restoration of the ylid moiety with aqueous weak base.

Alternatively, ozonolysis of the chlorides (5) gives the chlorothioester (8) which is transformed into the ylid (7) by means of triphenyl phosphine and a base.

Finally, compound (1a) or (1b) is simply obtained by heating the ylid (7) at a temperature ranging from 30° to 140° C. in an inert solvent such as benzene, toluene, or xylene.

The exocyclic (1a) or endocyclic (1b) position of the double bond depends upon a balance of the electron-withdrawing capacity of the COOR and R$^1$ groups, in association with ring strain release factors of the system.

Careful selective reduction of the α,β-unsaturated ester group of (1a,R$^1$=COOEt) allows one to obtain the hydroxymethyl-group (1a, R$^1$=CH$_2$OH) as in the clavulanic acid framework (P. H. Bentley, P. D. Berry, G. Brooks, M. L. Gilpin, E. Hunt, and I. I. Zomaya, *J.C.S. Chem. Comm.*, 1977, 748).

Additional irradiation of (1a, R$^1$=CH$_2$OH) in dry benzene allows the E/Z interconversion.

The following non-limiting examples serve still better to illustrate the invention:

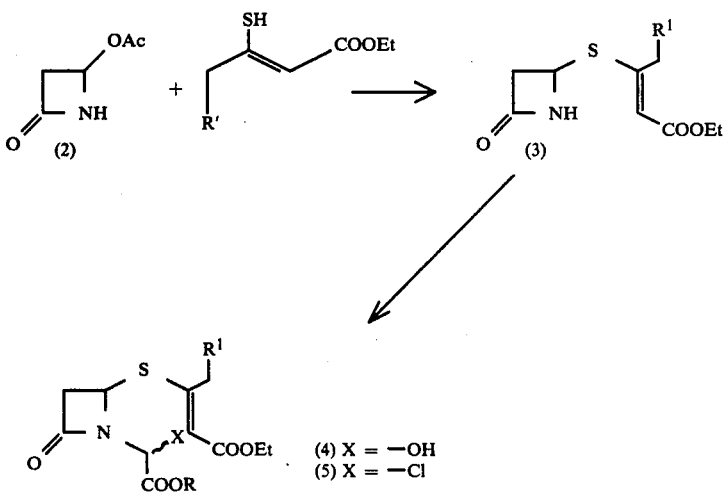

-continued

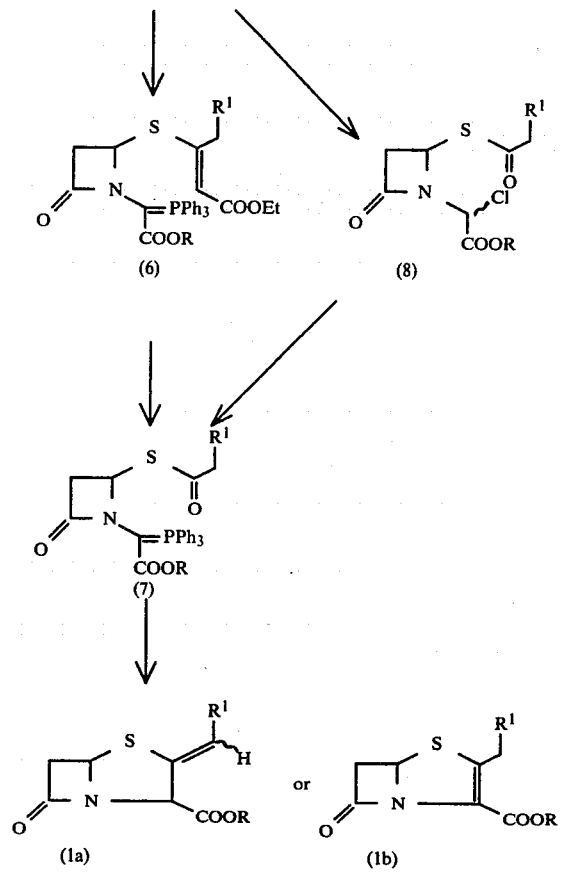

EXAMPLE 1

Diethyl 3-thio pentandioate.

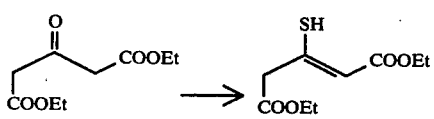

To absolute ethanol (170 ml), thoroughly saturated with anhydrous HCl at 0° C. (2 hrs.-2½ hrs.), was added diethyl 3-oxopentandioate (15 ml). The solution was cooled to −30° C. and saturated with H₂S. The reaction vessel was tightly stoppered and kept at room temperature during 48 hours. The reaction mixture was poured into brine and thoroughly extracted with a 1:1 mixture of diethyl ether and hexane. The organic layer was washed with brine to neutral, dried on Na₂SO₄, and evaporated in vacuo to yield a residue which was purified by short column chromatography on silica gel, eluting with 5% ethyl acetate-hexane.

P.M.R. (CDCl₃, δ):1.30 (6 H, t, J=7 Hz); 3.33 (2 H, s); 4.17 (4 H, q, J=7 Hz); 5.94 (1 H, s); 6.44 (1 H, s).

EXAMPLE 2

(4 R,S)-4-Vinylthio-(1-ethoxycarbonylmethyl-2-ethoxycarbonyl)-2-oxo-azetidine.

To a mixture of 4-acetoxy-2-oxo-azetidine (936 mg, 7.25 mmole) and of diethyl 3-thio-pentandioate (1.58 g, 7.25 mmole) in acetone (60 ml) and H₂O (30 ml) was added NaHCO₃ (670 mg, 8 mmole) with stirring at room temperature. After 1 hour additional stirring, the solution was saturated with NaCl, acidified with dilute HCl solution, and extracted with ethyl acetate (3 times). The combined extracts were washed with brine to neutral, dried on Na₂SO₄, and evaporated in vacuo to yield an oily residue. Column chromatography (silica gel) yielded the product as a colorless oil (1.94 g, 6.75 mmole, 93%).

P.M.R. (CDCl₃, δ):1.27 (6 H, t, J=7 Hz); 3.00 (1 H, dq, J₁=16 Hz, J₂=2.5 Hz, J₄=1.0 Hz); 3.53 (1 H, dq, J₁=16 Hz, J₃=5 Hz, J₄=1.5 Hz); 3.83 (2 H, s); 4.17 (2 H, q, J=7 Hz); 4.18 (2H, q, J=7 Hz); 5.13 (1 H, dd, J₂=2.5 Hz, J₃=5 Hz); 5.78 (1 H, s); 7.42 (1 H, br).

I.R. (CHCl₃, cm⁻¹): 3420, 1785, 1730, 1710, 1605, 1160.

EXAMPLE 3

Methyl-2-[(4 R,S)-4-vinylthio-(1-ethoxycarbonylmethyl-2-ethoxycarbonyl)-2-oxo-acetidin-1-yl]-2-hydroxy acetate.

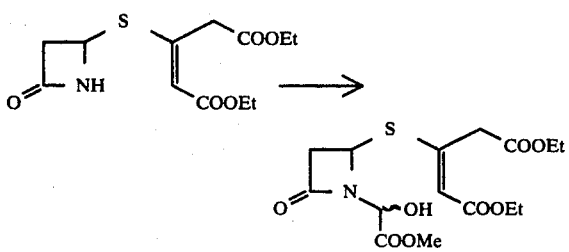

To (4 R,S)-4-vinylthio-(1-ethoxycarbonylmethyl-2-ethoxycarbonyl)-2-oxo-azetidine (926 mg, 3.2 mmole) and triethylamine (3.2 mmole, 0.450 ml) dissolved in anhydrous THF, was added a molar excess of methyl glyoxylate drop-wise. The reaction mixture was stirred in the presence of a molecular sieve at room temperature during 3 hours. The reaction mixture was then diluted with ethyl acetate, washed with NaHCO$_3$ saturated solution and brine, dried on Na$_2$SO$_4$, and evaporated in vacuo.

Treatment of the oily residue with diethyl ether yielded one of the two diastereoisomers as white crystals (560 mg).

P.M.R. (CDCl$_3$, δ):1.26 (6 H, t, j=7 Hz); 3.07 (1 H, dd, J$_1$=15 Hz, J$_2$=3 Hz); 3.53 (1 H, dd, J$_1$=15 Hz, J$_3$=5 Hz); 3.91 (3 H, s); 4.17 (2 H, q, J=7 Hz); 4.21 (2 H, q, J=7 Hz); 5.29 (2 H, d+dd, J$_2$=3 Hz, J$_3$=5 Hz); 5.97 (1 H, s).

The mother liquor, after concentration and purification by short column chromatography (SiO$_2$), yielded the other crystalline diastereoisomer (490 mg).

P.M.R. (CDCl$_3$, δ):1.27 (6 H, t, J=7 Hz); 3.14 (1 H, dd, J$_1$=15 Hz, J$_2$=3 Hz); 3.59 (1 H, dd, J$_1$=15 Hz, J$_3$=5 Hz); 3.82 (3H, s); 4.12 (2 H, q, J=7 Hz); 4.13 (2 H, q, J=7 Hz); 4.48 (1 H, d, J=6 Hz); 5.27 (1 H, dd, J$_2$=3 Hz, J$_3$=5 Hz); 5.49 (1 H, d, J=6 Hz); 5.88 (1 H, s). The total yield in the two carbinols was 88%.

EXAMPLE 4

Methyl-2-[(4 R,S)-4-vinylthio-(1-ethoxycarbonylmethyl-2-ethoxycarbonyl)-2-oxo-azetidin-1-yl]-2-chloroacetates.

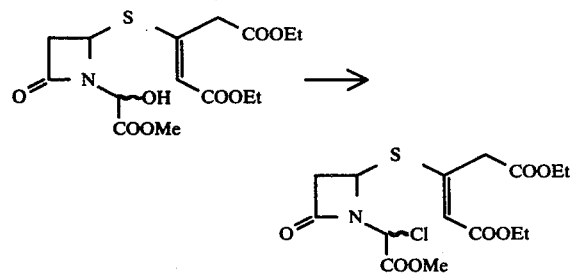

To the diastereoisomeric mixture of methyl 2-[(4R,S)-4-vinylthio-(1-ethoxycarbonylmethyl-2-ethoxycarbonyl)-2-oxo-azetidin-1-yl]-2-hydroxy-actates (500 mg, 1.33 mmole) and pyridine (0.28 ml, 3.5 mmole) dissolved in anhydrous THF, was added thionyl chloride (2.7 mmole) drop-wise at −30° C. under N$_2$. After 30 minutes of additional stirring at −30° to 0° C., the precipitate was filtered off, the filtrate was evaporated in vacuo at room temperature, the residue taken up with 50% AcOEt-C$_6$H$_6$ and rapidly eluted through a short column (SiO$_2$). 491 mg (1.25 mmole, 94%) of a yellow oil were collected.

P.M.R. (CDCl$_3$, δ):1.28 (6 H, t, J=7 Hz); 3.20 (1 H, dd); 3.67 (1 H, dd); 3.87 (3 H, s); 4.18 (4 H, q, J=7 Hz); 5.37 and 5.62 (1 H, dd); 5.88 (1 H, s); 6.12 and 6.20 (1 H, s).

EXAMPLE 5

Methyl-2-[(4R,S)-4-vinylthio-(1-ethoxycarbonylmethyl-2-ethoxycarbonyl)-2-oxo-azetidin-1-yl]-2-triphenylphosphoranylidene acetate.

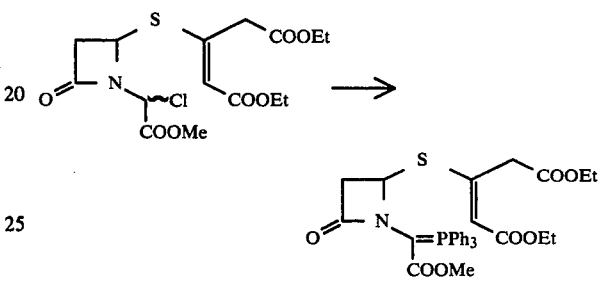

A mixture of methyl-2-[(4R,S)-4-vinylthio-(1-ethoxycarbonylmethyl-2-ethoxycarbonyl)-2-oxo-azetidin-1-yl]-2-chloroacetates (200 mg, 0.51 mmole), triphenylphosphine (262 mg, 1 mmole), and pyridine (0.041 ml) dissolved in anhydrous THF (6 ml), was stirred under N$_2$ at 30°–50° C. during 48 hours. The precipitate was filtered off and the filtrate was concentrated in vacuo and purified by preparative TLC. The ylid (246 mg, 0.35 mmole, 70%) was obtained as a white foam.

EXAMPLE 6

Methyl-2-[(4R,S)-4-ethoxycarbonylacetylthio-2-oxoazetidin-2-yl]-2-chloroacetates.

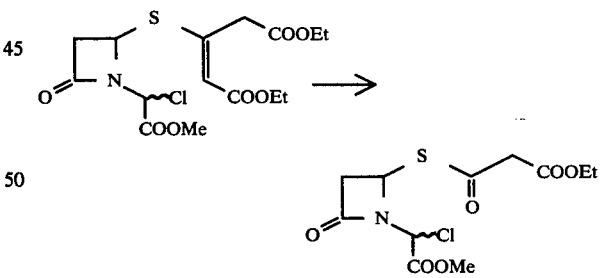

A solution of methyl-2-[(4R,S)-4-vinylthio-(1-ethoxycarbonylmethyl-2-ethoxycarbonyl)-2-oxo-azetidin-1-yl]-chloroacetates (491 mg, 1.25 mmole) in CH$_2$Cl$_2$ (80 ml), was cooled to −78° C. and ozonized. The resulting blue solution was stirred with sodium metabisulphite (2 hrs., room temperature), then washed with H$_2$O and dried on Na$_2$SO$_4$. The solvent was evaporated in vacuo and the resulting residue was purified by preparative TLC. A water-clear oil (165 mg, 0.51 mmole, 41%) was isolated.

P.M.R. (CDCl$_3$, δ):1.30 (3 H, s, J=7 Hz); 3.00, 3.23 and 3.45 (2 H, m); 3.63 (2 H, s); 3.83 and 3.90 (3 H, s); 4.22 (2 H, q, J=7 Hz); 5.75 (1 H, m); 6.08 (1 H, s).

EXAMPLE 7

Methyl-2-[(4 R,S)-4-ethoxycarbonylacetylthio-2-oxo-azetidin-1-yl]-2-triphenylphosphoranylidene acetate.

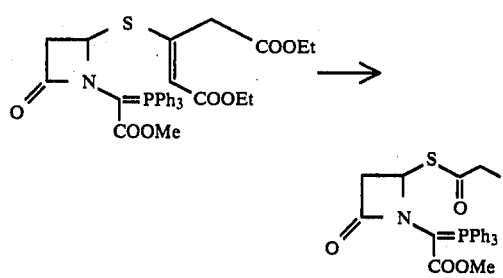

Methyl-2-[(4 R,S)-4-vinylthio-(1-ethoxycarbonyl-methyl-2-ethoxycarbonyl)-2-oxo-azetidin-1-yl]-2-triphenylphosphoranylidene acetate (246 mg, 0.35 mmole) dissolved in methylene chloride (15 ml) and a 10% v/v CF₃COOH solution in methylene chloride (18 ml) were mixed together, cooled to −20° C. and ozonized during 2½ minutes. Sodium metabisulfite was added with stirring to the foregoing solution, while the temperature was allowed to reach the ambient temperature. After 1 hour additional stirring, the suspension was filtered off, the filtrate washed with saturated NaHCO₃ solution, water, and then dried on NaSO₄. The solvent was evaporated to yield the title compound quantitatively.

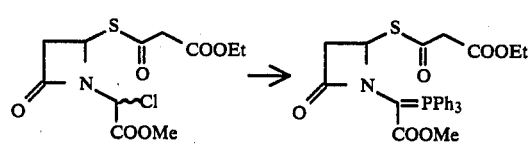

Alternatively, the title compound was obtained from methyl-2-[4 R,S)-4-ethoxycarbonylacetylthio-2-oxo-azetidin-1-yl]-2-chloroacetates with a procedure similar to that given in Example 6.

EXAMPLE 8

Methyl(±)-3-ethoxycarbonylmethylene-7-oxo-4-thia-1-azabicyclo-[3,2,0]-heptane-2-carboxylate

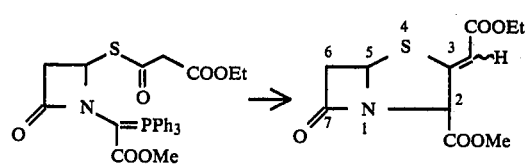

90 mg of methyl-2-[(4 R,S)-4-ethoxycarbonylacetylthio-2-oxo-azetidin-1-yl]-2-triphenylphosphoranylidene acetate, dissolved in toluene (3 ml) was heated at reflux during 30 minutes. The cooled reaction mixture was concentrated in vacuo and the residue purified by preparative TLC.

I.R. (CHCl₃, cm⁻¹):1795, 1755, 1700, 1600.

EXAMPLE 9

Benzyl-2-[(4 R,S)-4-vinylthio-(1-ethoxycarbonylmethyl-2-ethoxycarbonyl)-2-oxo-azetidin-1-yl]-2-hydroxyacetates.

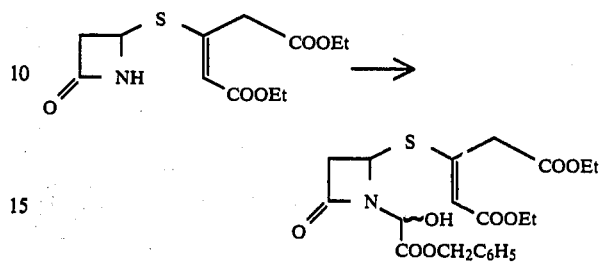

The title compounds were obtained as a diastereoisomeric mixture with a procedure similar to that given in Example 3. Elution with 5%–10% ethylacetate-benzene from an SiO₂ column yielded the oily products in 84% yield.

P.M.R. (CDCl₃, δ):1.27 (6 H, t, J=7 Hz); 2.87, 3.14 and 4.00 (2 H, m); 3.77 and 3.80 (2 H, s); 4.15 (4 H, q, J=7 Hz); 4.53 (1 H, d, J=8 Jz); 5.24 (4 H, m); 5.83 (1 H, s); 7.35 (5 H, s).

I.R. (CHCl₃, cm⁻¹):3530, 1780, 1750, 1710, 1600.

EXAMPLE 10

Benzyl-2-[(4 R,S)-4-vinylthio-(1-ethoxycarbonylmethyl-2-ethoxycarbonyl)-2-oxo-azetidin-1-yl]-2-chloroacetates.

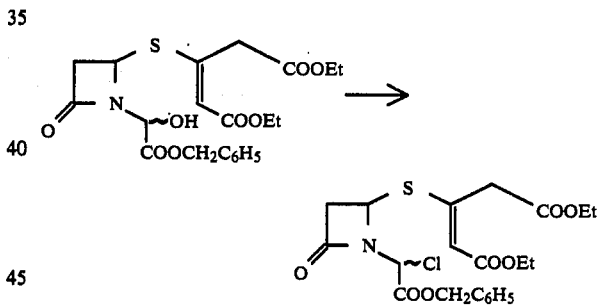

The title compound was obtained with a procedure similar to that given in Example 4 in 72% yield after short column chromatography (SiO₂).

P.M.R. (CDCl₃, δ):1.28 (6 H, s, J=7 Hz); 3.12 (1 H, dd); 3.65 (1 H, dd); 3.80 (2 H, s); 4.18 (4 H, q, J=7 Hz) 5.24 and 5.28 (2 H, s); 5.53 (1 H, m); 5.82 (1 H, s); 6.12 and 6.18 (1 H, s); 7.33 (5 H, s).

I.R. (CHCl₃, cm⁻¹):1790, 1750, 1710, 1600.

EXAMPLE 11

Benzyl-2-[(4 R,S)-4-vinylthio-(1-ethoxycarbonylmethyl-2-ethoxycarbonyl)-2-oxo-azetidin-1-yl]-2-triphenylphosphoranylidene acetate.

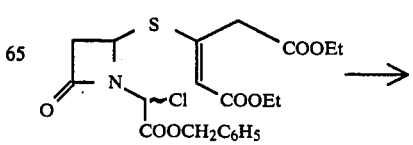

-continued

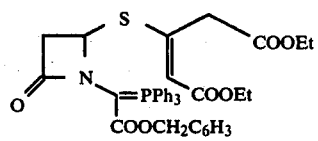

The title compound was obtained in 77% yield after column chromatography (SiO₂, 30% ethyl acetate-benzene) with a procedure similar to that given in Example 5.

EXAMPLE 12

Benzyl-2-[(4 R,S)-4-ethoxycarbonylacetylthio-2-oxo-azetidin-1-yl]-2-chloroacetates.

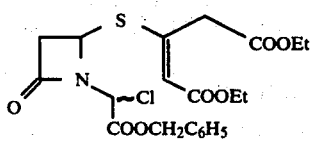

The title compound was obtained with a procedure similar to that given in Example 6.

P.M.R. (CDCl₃, δ):1.27 (3 H, t, J=7 Hz); 3.08 (1 H, dm); 3.54 and 3.58 (2 H, s); 3.60 (1 H, dm); 4.20 (2 H, q, J=7 Hz); 5.23 and 5.30 (2 H, s); 5.72 (1 H, m); 6.12 (1 H, s); 7.40 (5 H, s).

EXAMPLE 13

Benzyl-2-[(4 R,S)-4-ethoxycarbonylacetylthio-2-oxo-azetidin-1-yl]-2-triphenylphosphoranylidene acetate.

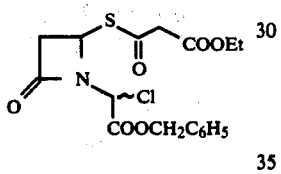

The title compound was obtained with a procedure similar to that given in Example 7.

I.R. (CHCl₃, cm⁻¹):1750, 1690, 1620.

EXAMPLE 14

Benzyl(±)-3-ethoxycarbonylmethylene-7-oxo-4-thia-1-azabicyclo-[3,2,0]-heptane-2-carboxylate.

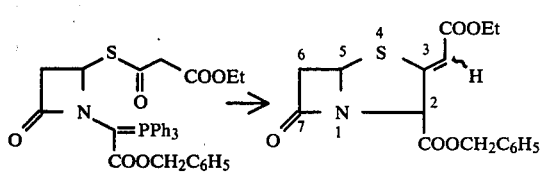

Benzyl-2-[(4 R,S)-4-ethoxycarbonylacetylthio-2-oxo-azetidin-1-yl]-2-triphenylphosphoranylidene acetate (195 mg, 0.31 mmole) dissolved in toluene (5 ml) was heated at reflux during 2½ hours under N₂. The cooled solution, concentrated in vacuo, was purified by preparative TLC and yielded the title product as an oil (88 mg, 0.254 mmole, 82% yield).

P.M.R. (CDCl₃, δ):1.28 (3 H, s, J=7 Hz); 3.20 (1 H, dd, J₁=16 Hz, J₂=2 Hz); 3.70 (1 H, dd, J₁=16 Hz, J₃=4 Hz); 4.22 (2 H, q, J=7 Hz); 5.20 (2 H, s); 5.36 (1 H, dd, J₃=4 Hz, J₂=2Hz); 5.53 (1 H, d, J=1.2 Hz); 6.14 (1 H, d, j=1.2 Hz); 7.37 (5 H, s). I.R. (CHCl₃, cm⁻¹):1795, 1755, 1700, 1600.

EXAMPLE 15

Ethyl-3-thio-5-hydroxy-pentanoate

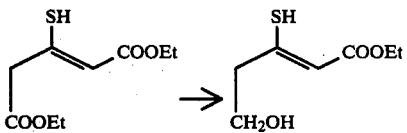

To a stirred solution of diethyl 3-thio-pentandioate (4.425 g, 20.3 mmole) in anhydrous THF (70 ml) cooled to −30° C. was added LiAlH₄ (920 mg, 25.5 mmole) in small portions under N₂. The resulting greenish slurry, after 1 hour of additional stirring, was decomposed with a 1 N HCl solution and extracted with diethyl ether (3 times). The combined extracts were washed with brine (3 times), dried (Na₂SO₄), and evaporated in vacuo to give a residue which was purified by column chromatography (SiO₂, elution with 20–25% ethyl acetate-hexane).

P.M.R. (CDCl₃, δ):1.30 (3 H, t, J=7 Hz); 2.60 (2 H+1 H, br t, J=6 Hz); 3.80 (2 H, t, J=6 Hz); 4.14 (2 H, q, J=7 Hz); 5.87 (1 H, s); 6.47 (1 H, s).

EXAMPLE 16

(4 R,S)-4-Vinylthio-(1-hydroxyethyl-2-ethoxycarbonyl)-2-oxo-azetidine.

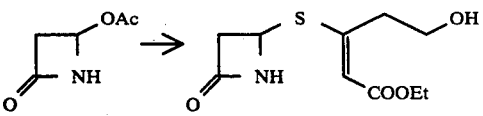

To a mixture of 4-acetoxy-2-oxo-azetidine (1.100 g, 8.5 mmole) and ethyl 3-thio-5-hydroxy-pentanoate (1.525 g, 8.66 mmole) in acetone (80 ml) and H₂O (40 ml) was added NaHCO₃ (766 mg, 9.15 mmole) with stirring at room temperature. Following the same procedure given in Example 2, 1.8 g (7.3 mmole, 86%) of a thick oil were obtained via column chromatography (SiO$_2$, elution with 40–50% ethyl acetate-benzene).

P.M.R. (CDCl$_3$, δ):1.32 (3 H, t, J=7 Hz); 2.97 (2 H+1 H, br t, J=6 Hz); 3.07 (1 H, m, J=16 Hz); 3.50 (1 H, dd, J$_1$=16 Hz, J$_3$=5 Hz); 3.85 (2 H, t, J=6 Hz); 4.17 (2 H, q, J=7 Hz); 5.07 (1 H, dd, J$_3$=5 Hz, J$_2$=2.5 Hz); 5.63 (1 H, s);

7.17 (1 H, br).

EXAMPLE 17

(4 R,S)-4-Vinylthio-(1-acetoxyethyl-2-ethoxycarbonyl)-2-oxo-azetidine

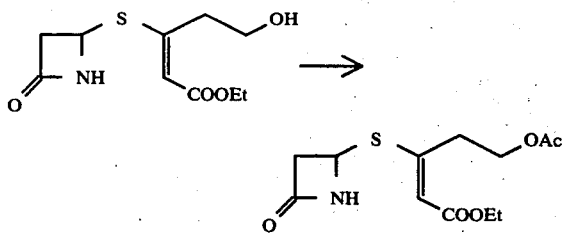

A mixture of (4 R,S)-4-vinylthio-(1-hydroxyethyl-2-ethoxycarbonyl)-2-oxo-azetidine (1.01 g, 4.13 mmole), acetic anhydride (1 ml, 10.6 mmole), and Et$_3$N (0.7 ml, 5 mmole) dissolved in methylene chloride (60 ml) was allowed to stand overnight at room temperature. The reaction mixture was then washed with brine (3 times), and dried on Na$_2$SO$_4$. Evaporation of the solvent left a residue which, after column chromatography (SiO$_2$, 10% ethyl acetate-benzene), yielded 950 mg (3.31 mmole, 81%) of an oily product.

P.M.R. (CDCl$_3$, δ):1.30 (3 H, t, J=7 Hz); 2.05 (3 H, s); 3.02 (1 H, dd, J$_1$=16 Hz); 3.12 (2 H, t, J=6 Hz); 3.52 (1 H, dd, J$_1$=16 Hz, J$_3$=5 Hz); 4.17 (2 H, t, J=6 Hz); 4.27 (2 H, q, J=7 Hz); 5.07 (1 H, dd, J$_3$=5 Hz, J$_2$=2.5 Hz); 5.60 (1 H, s); 7.38 (1 H, br).

EXAMPLE 18

Methyl-2-[(4 R,S)-4-vinylthio-(1-acetoxyethyl-2-ethoxycarbonyl)-2-oxo-azetidin-1-yl]-2-hydroxyacetates.

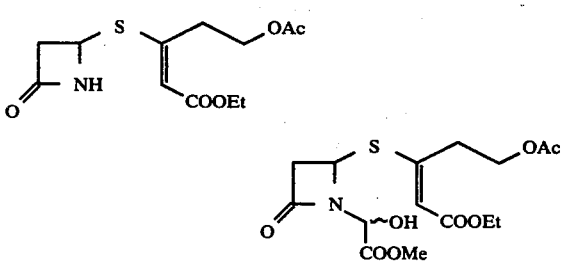

The title compound, as a diastereoisomeric mixture, was obtained in 87% yield after column chromatography (SiO$_2$, elution 25% ethyl acetate-benzene), by a procedure similar to that given in Example 3.

P.M.R. (CDCl$_3$, δ):1.27 (3 H, t); 2.01 (3 H, s); 3.01 and 3.44 (4 H, m); 3.83 and 3.87 (3 H, s); 4.15 (4 H, m); 5.21 (2 H, m); 5.71 and 5.73 (1 H, s).

EXAMPLE 19

Methyl-2-[(4 R,S)-4-vinylthio-(1-acetoxyethyl-2-ethoxy-carbonyl)-2-oxo-azetidin-1-yl]-2-chloroacetates.

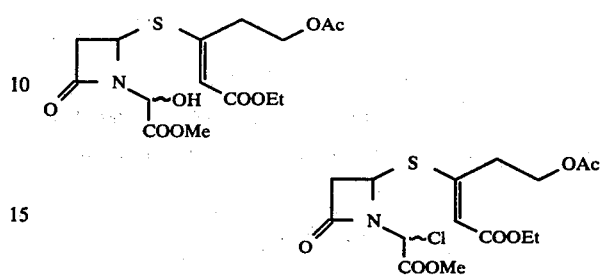

The title compound, as diastereoisomeric mixture, was obtained in 52% yield after preparative TLC by a procedure similar to that given in Example 4.

P.M.R. (CDCl$_3$, δ):1.28 (3 H, t); 2.05 (3 H, s); 3.16 and 3.60 (4 H, m); 3.82 and 3.87 (3 H, s); 4.17 (2 H, t); 4.28 (2 H, t); 5.32 and 5.55 (1 H, dd); 5.68 (1 H, s); 6.08 and 6.13 (1 H, s).

EXAMPLE 20

Methyl-2-[(4 R,S)-4-vinylthio-(1-acetoxyethyl-2-ethoxycarbonyl)-2-oxo-azetidin-1-yl]-2-triphenylphosphoranylidene acetate.

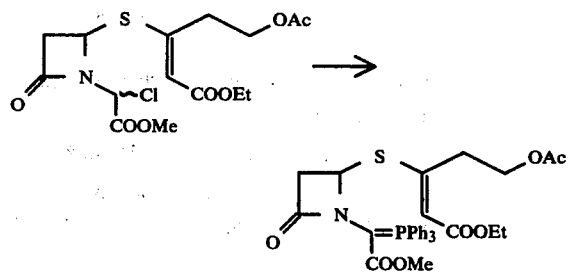

The title compound was obtained in 68% yield, after preparative TLC, by a procedure similar to that given in Example 5.

EXAMPLE 21

Methyl-2-(4 R,S)-4-acetoxymethylacetylthio-2-oxo-azetidin-1-yl]-2-triphenylphosphoranylidene acetate.

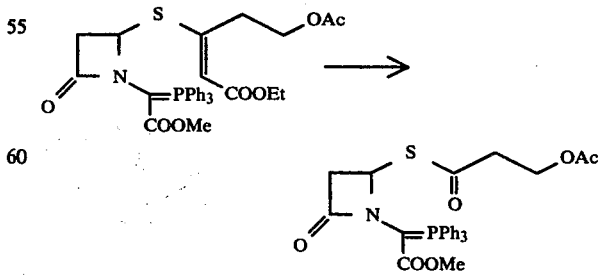

The title compound was obtained in quantitative yield with a procedure similar to that given in Example 7.

EXAMPLE 22

Methyl(±)-2-acetoxyethyl-2-penem-3-carboxylate

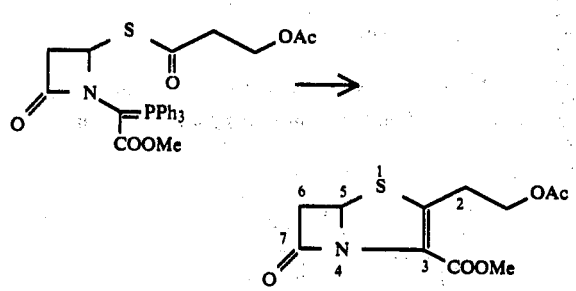

Methyl-2-[(4 R,S)-4-acetoxymethylacetylthio-2-oxo-azetidin-1-yl]-2-triphenylphosphoranylidene acetate (100 mg) dissolved in toluene (5 ml) was heated at reflux during 2 hours. Subsequent preparative TLC afforded the title compound in 61% yield.

P.M.R. (CDCl$_3$, δ):2.04 (3 H, s); 3.21 (2 H, t, J=6 Hz); 3.46 (1 H, dd, J$_1$=16 Hz, J$_2$=2 Hz); 3.77 (1 H, dd, J$_1$=16 Hz, J$_3$=4 Hz); 3.83 (3 H, s); 4.09 (2 H, t, J=6 Hz); 5.64 (1 H, dd, J$_2$=2 Hz, J$_3$=4 Hz).

I.R. (CHCl$_3$, cm$^{-1}$):1795, 1740, 1710, 1520.
U.V. (EtOH, nm):263, 317.

EXAMPLE 23

Acetoxymethyl-2-[(4 R,S)-4-vinylthio-(1-ethoxycarbonyl-methyl-2-ethoxycarbonyl)-2-oxo-azetidin-1-yl]-2-hydroxyacetates

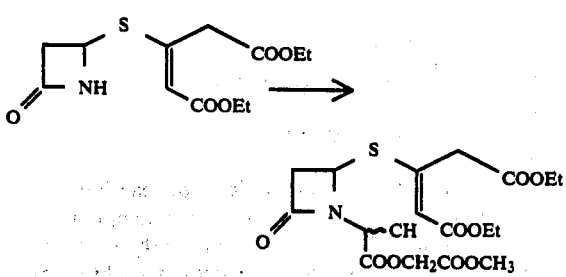

A mixture of (4 R,S)-4-vinylthio-(1-ethoxycarbonyl-methyl-2-ethoxycarbonyl)-2-oxo-azetidine (2.392 g, 8.35 mmole) and acetoxymethyl glyoxylate (4 g, freshly prepared by ozonolysis of the corresponding fumarate) in benzene (80 ml) was refluxed through a Dean-Stark trap during 4 hours. The cooled reaction mixture was poured on top of a silica gel column. Elution with 10% ethyl acetate-benzene yielded the title product as a diastereoisomeric mixture (3.10 g, 7.15 mmole, 88.2%).

EXAMPLE 24

Acetoxymethyl-2-[(4 R,S)-4-vinylthio-(1-ethoxycarbonylmethyl-2-ethoxycarbonyl)-2-oxo-azetidin-1-yl]-2-chloroacetates

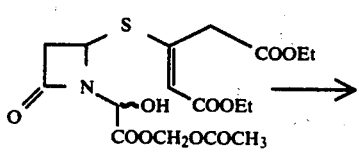

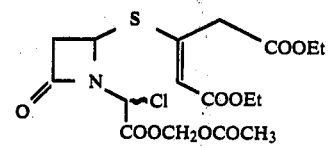

To the diastereoisomeric mixture of acetoxymethyl-2-(4 R,S)-4-vinylthio-(1-ethoxycarbonylmethyl-2-ethoxycarbonyl)-2-oxo-azetidin-1-yl]-2-hydroxyacetates (611 mg, 1.4 mmole) and pyridine (0.30 ml) dissolved in anhydrous THF was added thionyl chloride (2.8 mmole dissolved in 10 ml of THF) drop-wise at −30° C. under N$_2$. After 20 minutes stirring, the reaction mixture was poured into water and extracted with ethyl acetate (3 times). The combined extracts were washed with brine (4 times) and dried (Na$_2$SO$_4$). Evaporation of the solvent in vacuo yielded the diastereoisomeric chlorides as a yellowish oil (563 mg, 1.24 mmole, 89% yield).

P.M.R. (CDCl$_3$, δ):1.30 (6 H, t, J=7 Hz); 2.03 and 2.05 (3 H, s); 3.03, 3.32 and 3.60 (2 H, m); 3.85 and 3.87 (2 H, s); 4.17 and 4.19 (4 H, q, J=7 Hz); 5.35 and 5.56 (1 H, q); 5.85, 5.89 and 5.91 (2 H+1 H, s); 6.08 and 6.15 (1 H, s).

EXAMPLE 25

Acetoxymethyl-2-[(4 R,S)-4-vinylthio-(1-ethoxycarbonylmethyl-2-ethoxycarbonyl)-2-oxo-azetidin-1-yl]-2-triphenylphosphoranylidene acetate.

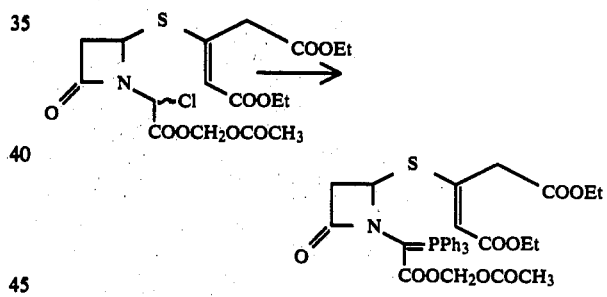

The title compound was obtained in 71% yield after column chromatography (SiO$_2$, 25% ethyl acetate-benzene) with a procedure similar to that given in Example 5.

EXAMPLE 26

Acetoxymethyl-2-[(4 R,S)-4-ethoxycarbonylacetylthio-2-oxo-azetidin-1-yl]-2-triphenylphosphoranylidene acetate

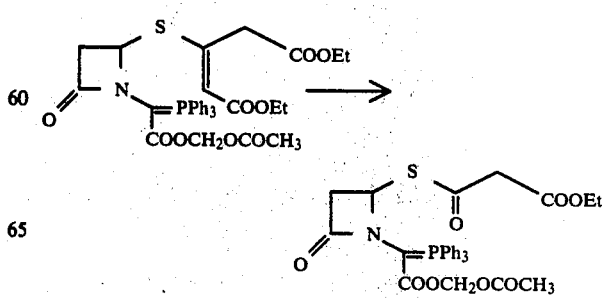

The title compound was obtained with a procedure similar to that given in Example 7.

EXAMPLE 27

Acetoxymethyl($\pm$)-3-ethoxycarbonylmethylene-7-oxo-4-thia-1-azabicyclo-[3,2,0]-heptane-2-carboxylate.

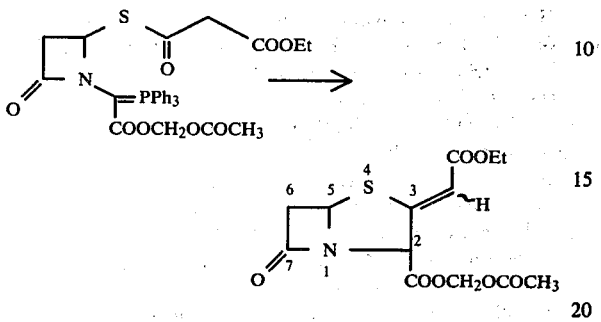

Acetoxymethyl-2-[(4 R,S)-4-ethoxycarbonylacethylthio-2-azetidin-1-yl]-2-triphenylphosphoranylidene acetate (665 mg, 1.10 mmole) dissolved in toluene (20 ml) was heated at reflux during 4 hours under $N_2$. The cooled solution was poured on top of a silica gel column. Elution with 5% ethyl acetate-benzene afforded an oily product (250 mg, 0.78 mmole, 71%).

P.M.R. ($CDCl_3$, $\delta$): 1.32 (3 H, s, J=7 Hz); 2.30 (E H, s); 3.23 (1 H, dd, $J_1$=16 Hz, $J_2$=2 Hz); 3.82 (1 H, dd, $J_1$=16 Hz, $J_3$=4 Hz); 4.26 (2 H, q, J=7 Hz); 5.42 (1 H, dd, $J_3$=4 Hz, $J_2$=2 Hz); 5.55 (1 H, d, J=1.2 Hz); 5.82 (2 H, s); 6.18 (1 H, d, J=1.2 Hz).

What is claimed is:

1. A process for the preparation of compounds of formula I:

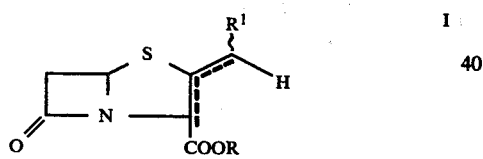

wherein R is hydrogen, lower alkyl, trichloroethyl, benzyl, p-nitrobenzyl, acetoxymethyl, pivaloyloxymethyl, phthalidyl, or a —CH(CH₃) OCOOEt group;

$R^1$ is —$CH_2OH$, —CHO, —$CH_3SH$, —$CH_2NH_2$, —$CH_2OCOR^2$, —$COOR^2$, —$CH_2NHCOR^2$, or —$CH_2OR^3$, where $R^2$ is a lower alkyl, and $R^3$ is a lower alkyl, benzyl, or trityl, which comprises reacting a 4-acetoxy azitidinone of formula II:

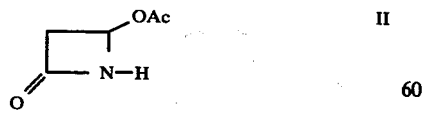

dissolved in a solvent selected from the group consisting of acetone, tetrahydrofuran, dimethylformamide, water, and mixtures thereof, at room temperature and in the presence of a base selected from the group consisting of $NaHCO_3$, KOH, $K_2CO_3$, and $Et_3N$, with a $\beta$-thioketoester of formula:

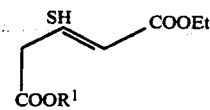

where $R^1$ has the meanings given above, to obtain a mixture of diastereoisomeric products of formula III;

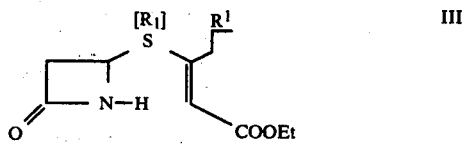

where $R^1$ is as above defined, which mixture is successively condensed, dissolved in anhydrous acetone and in the presence of a base selected from the group consisting of pyridine and triethylamine, at room temperature, with a glyoxylic ester of formula:

where R has the meanings given above, to give a mixture of diastereoisomeric substituted carbinols of formula IV:

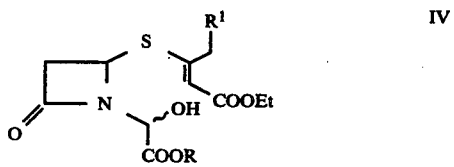

where R and $R^1$ are as above defined, reacting that mixture with thionyl chloride, at a temperature ranging from $-78°$ C. to $0°$ C. and in the presence of pyridine, to afford the corresponding chlorides of formula V:

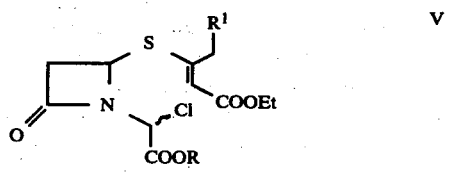

which are transformed by means of triphenylphosphine and a base selected from the group consisting of pyridine and 2,6-lutidine, at a temperature of $25°-50°$ C., into their respective phosphorous ylids of formula VI:

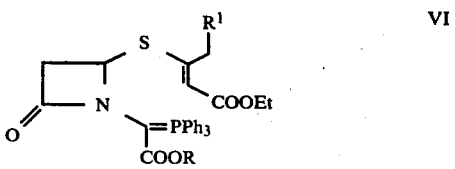

ozonolysing the compounds of formula VI in the presence of trifluoroacetic acid, to obtain the corresponding phosphoranes of formula VII:

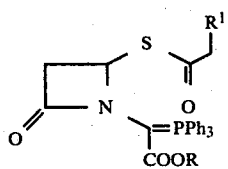

and successively heating the so-obtained phosphoranes of formula VII at a temperature ranging from 30° to 140° C., in an inert solvent selected from the group consisting of benzene, toluene, and xylene, to obtain the desired compounds of formula I.

2. A process for the preparation of compounds of formula I, which comprises first ozonolysing the substituted chlorides of formula V, prepared as described in claim 1, at a temperature of about −78° C. and in dichloromethane, to obtain substituted chlorothioesters of formula VIII:

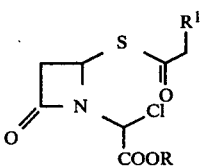

wherein R and $R^1$ have the meanings as defined in claim 1, which by means of triphenyl phosphine and a base are successively transformed into the substituted phosphoranes of formula VII, as defined in claim 1, from which the final products of formula I, according to the procedure described in claim 1, are finally obtained.

* * * * *

UNITED STATES PATENT AND TRADEMARK OFFICE
CERTIFICATE OF CORRECTION

PATENT NO. : 4,269,771 (Page 1 of 6)

DATED : May 26, 1981

INVENTOR(S) : Paolo LOMBARDI et al

It is certified that error appears in the above-identified patent and that said Letters Patent are hereby corrected as shown below:

Column 5, Example 3, line 5, change "acetidin" to -- azetidin --.

Column 5, Example 4, line 64, change "actates" to -- acetates --.

UNITED STATES PATENT AND TRADEMARK OFFICE
CERTIFICATE OF CORRECTION

PATENT NO. : 4,269,771
DATED : May 26, 1981
INVENTOR(S) : Paolo LOMBARDI et al

It is certified that error appears in the above-identified patent and that said Letters Patent are hereby corrected as shown below:

Column 13, Example 22, lines 11 thru 15, please change the formula

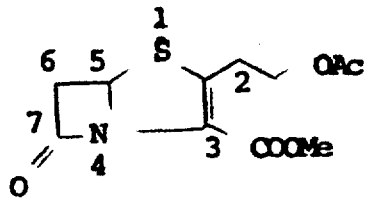

to:

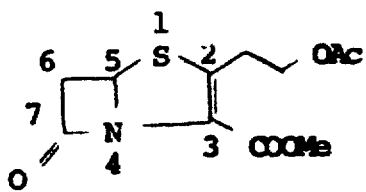

UNITED STATES PATENT AND TRADEMARK OFFICE
CERTIFICATE OF CORRECTION

PATENT NO. : 4,269,771 (Page 3 of 6)
DATED : May 26, 1981
INVENTOR(S) : Paolo LOMBARDI et al It is certified that error appears in the above-identified patent and that said Letters Patent are hereby corrected as shown below:

Column 13, Example 23, lines 40 thru 45, please change the formula

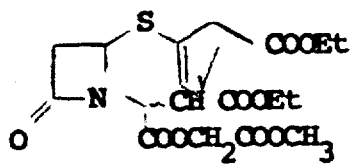

to:

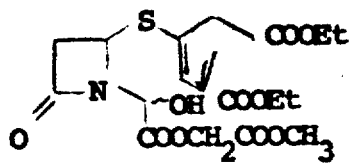

UNITED STATES PATENT AND TRADEMARK OFFICE
CERTIFICATE OF CORRECTION

PATENT NO. : 4,269,771 (Page 4 of 6)

DATED : May 26, 1981

INVENTOR(S) : Paolo LOMBARDI et al

It is certified that error appears in the above-identified patent and that said Letters Patent are hereby corrected as shown below:

Column 15, Example 27, line 21, change

"Acetoxymethyl-2-[(4 R,S)-4-ethoxycarbonylaceth-" to

-- Acetoxymethyl-2-[(4 R,S)-4-ethoxycarbonylacet- --.

Column 15, Claim 1, line 54, change "azitidinone" to -- azetidinone --.

UNITED STATES PATENT AND TRADEMARK OFFICE
CERTIFICATE OF CORRECTION

PATENT NO. : 4,269,771 (Page 5 of 6)
DATED : May 26, 1981
INVENTOR(S) : Paolo LOMBARDI et al It is certified that error appears in the above-identified patent and that said Letters Patent are hereby corrected as shown below:

Column 16, Claim 1, lines 1 thru 6, please change the formula

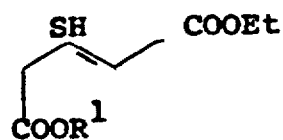

to:

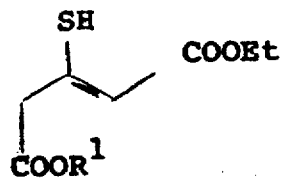

UNITED STATES PATENT AND TRADEMARK OFFICE
CERTIFICATE OF CORRECTION

PATENT NO. : 4,269,771

DATED : May 26, 1981

INVENTOR(S) : Paolo LOMBARDI et al

It is certified that error appears in the above-identified patent and that said Letters Patent are hereby corrected as shown below:

Column 16, Claim 1, lines 12 thru 17, please change the formula

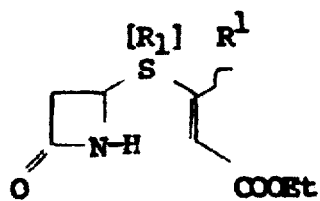

to:

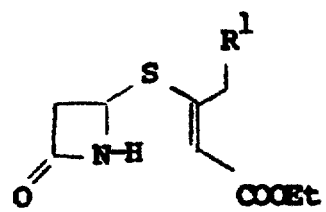

Signed and Sealed this

Twentieth Day of July 1982

[SEAL]

Attest:

GERALD J. MOSSINGHOFF

Attesting Officer

Commissioner of Patents and Trademarks

UNITED STATES PATENT AND TRADEMARK OFFICE
CERTIFICATE OF CORRECTION

PATENT NO. : 4,269,771
DATED : May 26, 1981
INVENTOR(S) : Paolo LOMBARDI et al

It is certified that error appears in the above-identified patent and that said Letters Patent are hereby corrected as shown below:

Column 16, Claim 1, lines 1 thru 6, please ignore the previous change request of May 4, 1982, and instead change the formula

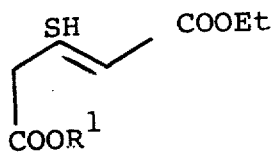

to:

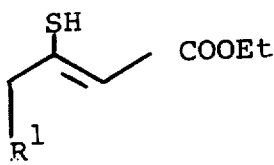

Signed and Sealed this

Twenty-fifth Day of September 1984

[SEAL]

Attest:

GERALD J. MOSSINGHOFF

Attesting Officer

Commissioner of Patents and Trademarks